United States Patent
Cason et al.

(10) Patent No.: US 8,685,688 B2
(45) Date of Patent: Apr. 1, 2014

(54) ISOLATION OF A PROTEIN RESPONSIBLE FOR URANIUM (VI) REDUCTION

(75) Inventors: Errol Duncan Cason, Bloemfontein (ZA); Esta Van Heerden, Bloemfontein (ZA); Lizelle Ann Piater, Johannesburg (ZA); Abitha Gyanendra Jugdave, Bloemfontein (ZA); Jacqueline Van Marwijk, Vanderbijlpark (ZA)

(73) Assignee: University of the Free State, Bloemfontein (ZA)

( * ) Notice: Subject to any disclaimer, the term of this patent is extended or adjusted under 35 U.S.C. 154(b) by 6 days.

(21) Appl. No.: 13/497,407

(22) PCT Filed: Sep. 21, 2010

(86) PCT No.: PCT/IB2010/054259
§ 371 (c)(1),
(2), (4) Date: Jul. 18, 2012

(87) PCT Pub. No.: WO2011/033491
PCT Pub. Date: Mar. 24, 2011

(65) Prior Publication Data
US 2012/0276610 A1    Nov. 1, 2012

(30) Foreign Application Priority Data
Sep. 21, 2009    (ZA) ........................ 09/6569

(51) Int. Cl.
*C12N 9/02*    (2006.01)
*C12N 1/20*    (2006.01)
*C12N 15/00*    (2006.01)
*C07H 21/04*    (2006.01)
*A61L 9/01*    (2006.01)

(52) U.S. Cl.
USPC .................. 435/189; 435/252.3; 435/252.33; 435/320.1; 435/262; 536/23.2

(58) Field of Classification Search
None
See application file for complete search history.

(56) References Cited

U.S. PATENT DOCUMENTS

2006/0014261 A1    1/2006    Phelps et al.

FOREIGN PATENT DOCUMENTS

WO    WO-93/13883 A1    7/1993

OTHER PUBLICATIONS

Slobodkin, A.I. "Thermophilic iron-reducing prokaryotes" *Dissertation Abstract*, Moscow, 2008, pp. 1-48.
Russian Office Action dated Sep. 3, 2013 in Russian Application No. 2012116151, filed Sep. 21, 2010.
van Heerden et al. "Metabolic promiscuity from the deep subsurface: a story of Survival or Superiority" *Proceedings of the SPIE*, Aug. 12, 2008, 7097:S-1-S12.
Lovley, D.R. et al. "Microbial reduction of uranium" *Letters to Nature*, Apr. 4, 1991, 350(6317):413-416.
Database UniProt [Online] Dec. 21, 2004, "SubName: Full=Peptide ABC transporter, peptide-binding protein;", XP002616797.
Database UniProt [Online] Jul. 5, 2004, "SubName: Full=Dipeptide-binding protein;", XP002616798.
International Search Report in International Application No. PCT/IB2010/054259, filed Sep. 21, 2010.

*Primary Examiner* — Nashaat Nashed
(74) *Attorney, Agent, or Firm* — Saliwanchik Lloyd & Eisenschenk

(57) ABSTRACT

The present invention relates to the isolation and characterization of a protein responsible for the reduction of uranium (VI) to uranium (IV). The present invention extends to the use of the isolated protein in the reduction of uranium (VI) to uranium (IV) and further extends to a process for the bioremediation, or at least partial remediation, of a site contaminated with a source of U (VI). According to a first aspect thereof, the present invention provides an isolated polypeptide derived from *Thermus scotoductus* strain SA-01 that is responsible for the reduction of uranium (VI), in a source of uranium (VI), to uranium (IV), wherein the polypeptide comprises the amino acid sequence of SEQ ID No: 1.

9 Claims, 10 Drawing Sheets

SEQUENCE LISTING

<160> NUMBER OF SEQ ID NOS: 2

<210> SEQ ID NO 1
<211> LENGTH: 626
<212> TYPE: PRT
<213> ORGANISM: Thermus scotoductus

<400> SEQUENCE: 1

```
Met Arg Lys Val Gly Lys Leu Ala Val Phe Gly Leu Ala Ala Leu Gly
1               5                   10                  15

Leu Ala Leu Ala Gly Pro Gln Asp Asn Ser Leu Val Ile Gly Ala Ser
            20                  25                  30

Gln Glu Pro Arg Val Leu Ala Gly Asp Phe Leu Ser Ile Ile Ser Asn
        35                  40                  45

Ser Ile Lys Leu Glu Ile Glu Gln Tyr Leu Phe Ala Pro Leu Ile
    50                  55                  60

Gly Phe Asn Ala Asn Ser Glu Asn Phe Pro Val Leu Val Thr Glu Val
65                  70                  75                  80

Pro Thr Arg Gln Asn Gly Arg Leu Arg Val Thr Asp Ile Gly Gly Gly
                85                  90                  95

Lys Lys Arg Leu Glu Met Asp Leu Thr Ile Arg Pro Asp Ala Arg Trp
            100                 105                 110

Ser Asp Gly Lys Pro Ile Thr Thr Glu Asp Val Ala Phe Tyr Tyr Glu
        115                 120                 125

Val Gly Lys Ala Lys Gly Met Pro Val Leu Asn Pro Tyr Trp Glu
    130                 135                 140

Arg Val Asn Leu Arg Val Arg Asp Ala Arg Asn Phe Thr Val Ile Phe
145                 150                 155                 160

Glu Pro Ala Tyr Tyr Tyr Asp Thr Tyr Gly Gly Thr Tyr Gly Ser Pro
                165                 170                 175

Ile Gly Tyr Ala Pro Lys His Ile Met Gly Ala Glu Trp Glu Lys Val
            180                 185                 190

Lys Ala Ala Ala Arg Asn Leu Asp Pro Asp Lys Asp Ala Glu Arg Leu
        195                 200                 205

Asn Glu Leu Tyr Arg Asn Phe Phe Leu Lys Phe Ala Thr Pro Gln Ala
    210                 215                 220

Leu Asn Arg Gly Ala Met Val Tyr Ser Gly Ala Phe Lys Leu Arg Arg
225                 230                 235                 240

Trp Val Pro Gly Asn Ser Ile Glu Met Glu Arg Asn Pro Asn Phe Pro
                245                 250                 255

Ile Lys Pro Glu Gly Gly Glu Ser Arg Tyr Val Gln Arg Val Val Tyr
            260                 265                 270

Arg Phe Ile Gln Asn Thr Asn Ser Leu Leu Val Ala Val Leu Gly Gly
        275                 280                 285

Ser Ile Asp Ala Thr Ser Ser Val Ser Leu Thr Phe Asp Gln Gly Arg
    290                 295                 300

Ser Arg Gln Leu Thr Ser Arg Ala Pro Gly Arg Phe Asp Ile Trp Phe
305                 310                 315                 320

Val Pro Gly Ala Ile Trp Glu His Ile Asp Val Asn Lys Phe Glu Asn
                325                 330                 335

Cys Gln Ala Val Arg Asp Leu Gly Leu Asn Asp Val Arg Thr Arg Arg
            340                 345                 350

Ala Leu Leu His Ala Leu Asn Arg Glu Gly Leu Val Lys Ala Phe Phe
        355                 360                 365
```

Asp Gly Leu Gln Pro Val Ala His Thr Trp Ile Ala Pro Val Asn Pro
    370                 375                 380

Leu Phe Asn Pro Asn Val Arg Lys Tyr Glu Phe Asp Leu Lys Lys Ala
385                 390                 395                 400

Glu Ala Leu Leu Ala Glu Met Gly Trp Arg Lys Gly Pro Asp Gly Ile
            405                 410                 415

Leu Gln Arg Thr Val Gly Gly Arg Thr Val Arg Phe Glu Ile Glu Phe
            420                 425                 430

Val Thr Thr Ala Gly Asn Ala Ile Arg Glu Arg Thr Gln Gln Phe Phe
            435                 440                 445

Ala Glu Asp Leu Lys Lys Ile Gly Ile Ala Val Lys Ile Asn Asn Ala
            450                 455                 460

Pro Ser Ala Val Val Phe Ala Asp Asp Tyr Ile Gln Arg Ala Ser Glu
465                 470                 475                 480

Cys Lys Trp Thr Gly Leu Phe Glu Phe Ala Trp Val Ser Asn Leu Ala
                485                 490                 495

Glu Asp Gly Ser Leu Phe Gln Tyr Lys Asn Leu Asn Thr Gly Ala Ile
            500                 505                 510

Met Val Pro Thr Lys Glu Asn Asn Tyr Gln Gly Gln Asn Ile Gly Gly
            515                 520                 525

Trp Arg Asn Asp Glu Phe Asp Arg Leu Thr Ser Gln Gly Val Leu Glu
530                 535                 540

Phe Asp Glu Ala Arg Arg Lys Gln Leu Phe Trp Arg Ala Gln Glu Ile
545                 550                 555                 560

Trp Ala Glu Glu Leu Pro Ala Leu Pro Leu Tyr Phe Arg Ala Asn Pro
                565                 570                 575

Tyr Val Val Arg Lys Gly Leu Val Asn Tyr Val Ala Ser Ala Tyr Ala
            580                 585                 590

Gly Gly Tyr Gly Tyr Pro Gly Trp Asn Ala Trp Glu Ile Gly Trp Glu
            595                 600                 605

Ser Arg Gly Ala Val Lys Lys Trp Asp Gln Ala Lys Tyr Ala Leu Ser
610                 615                 620

Val Lys
625

<210> SEQ ID NO 2
<211> LENGTH: 1881
<212> TYPE: DNA
<213> ORGANISM: Thermus scotoductus

<400> SEQUENCE: 2
atgagaaaag taggcaagct ggctgtattc ggtttagccg ccctgggctt ggccctggcg      60
gggccccagg acaacagcct ggtcataggg gcttcgcagg agccccgggt tctggcgggg     120
gacttcctaa gcatcatctc caaccagtcc atcaagttgg agatcgagca gtacctcttc     180 gccccccctca tcggtttcaa cgccaacagc gaaaactttc ccgtgctggt caccgaggtg     240
cccacccggc aaaacgggcg tttgcgggtg acggacatcg gcggggcaa gaagcgcttg     300 gagatggacc tcaccatccg gcccgatgcc cgctggtccg acggcaagcc catcaccacc     360
gaggatgtgg ccttctacta cgaggtgggc aaggccaagg gatgccggt gctcaacccg     420 gactactggg agcgggtgaa cctccgggtc agggacgccc gcaacttcac cgtgatcttt     480
gagcccgcct actactacga cacctacggg gcacctacg gctcccccat cggctacgct     540
cccaagcaca tcatgggcgc cgagtgggag aaggtgaaag cggcggcccg gaacctggat     600

-continued

```
cccgataagg atgcggagag gctcaacgag ctctaccgca acttcttcct caagttcgcc      660
actccccagg ccctaaaccg gggagccatg gtctactcgg gggccttcaa gctgcggcgc      720
tgggtgccgg ggaactccat tgagatggag cggaacccca acttccccat caagcccgag      780
ggtggggaga gccggtacgt gcagagggtg gtctaccgct tcatccagaa caccaactcc      840
ctcctggtgg ccgtcctggg cgggagcatt gacgccacct ccagcgtctc cctcaccttt      900
gaccaaggcc gtagccgcca gctcacctcc cgggcccctg gccgctttga catctggttc      960
gtgcccgggg ccatctggga gcacattgac gtcaacaagt ttgagaactg ccaggcggtc     1020
cgcgacttgg gcctgaacga cgtccgcacc cgtcgggccc tcctccacgc tctgaaccgc     1080
gaggggttgg tcaaggcctt ctttgacggc ctccagcccg tggcccacac ctggatcgcc     1140
cccgtcaacc ccctcttcaa ccccaatgtg cggaagtacg agtttgacct gaagaaggcg     1200
gaggcgctct tggcggagat gggctggagg aaggggccgg acggcatcct tcagcgcacc     1260
gtgggtggcc gcaccgtgcg ctttgagatt gagttcgtca ccaccgcggg caacgctatc     1320
cgggagcgca cccagcagtt cttcgccgag gacctgaaga agatcggcat cgccgtcaag     1380
atcaataacg cccccagcgc cgtggtcttc gccgacgact acatccagcg ggccagcgag     1440
tgcaagtgga ccgggctgtt tgagttcgct tgggtttcca acctggccga ggatggctcc     1500
ctcttccagt acaagaacct gaacaccggg gccatcatgg tgcccaccaa ggagaacaac     1560
taccaggggc agaacatcgg cggctggcgc aacgacgagt ttgaccgtct gacgagccag     1620
ggtgtcctgg agtttgacga ggccaggcgg aagcagctct tctggagggc ccaggagatc     1680
tgggccgagg agctgcctgc cttgcccctc tacttccgcg ctaacccta cgtggtgcgg     1740
aagggcctgg tcaactacgt ggccagcgct tacgcgggcg gctacggtta ccccggctgg     1800
aacgcttggg agatcggctg ggagagccgc ggcgccgtga agaagtggga ccaggcgaag     1860
tacgctcttt ccgtcaagta a                                              1881
```

ISOLATION OF A PROTEIN RESPONSIBLE FOR URANIUM (VI) REDUCTION

CROSS-REFERENCE TO RELATED APPLICATIONS

This application is the U.S. national stage application of International Patent Application No. PCT/IB2010/054259, filed Sep. 21, 2010, which claims priority to South African Application No. 2009/06569, filed Sep. 21, 2009, the disclosures of each of which are incorporated herein by reference in their entirety.

TECHNICAL FIELD

The present invention relates to the isolation and characterization of a protein responsible for the reduction of uranium (VI) to uranium (IV). The present invention extends to the use of the isolated protein in the reduction of uranium (VI) to uranium (IV) and further extends to a process for the bioremediation, or at least partial remediation, of a site contaminated with a source of U (VI).

BACKGROUND TO THE INVENTION

In the past decade, our concept of what conditions are compatible with life, have changed significantly. The earlier, anthropocentric view of nature has limited our capacity to access new microbes and their genomes, but the discovery that almost all environments on earth and even the subsurface (more than 4 km), or subzero temperatures and high levels of radiation are likely to contain specially adapted life forms, has made the notion to understand the microbial biodiversity very important.

One of the most amazing features of the microbial world is that even the most toxic and apparently recalcitrant of substances developed by (chemical) industry over the decades usually prove to be degradable by one micro-organism or another. Microorganisms can encounter a large variety of chemicals such as metals in contaminated environments, thus it is not surprising that they would interact with these metals (Nies and Sliver, 1995).

U (VI) resistant bacteria isolated from contaminated environments have been shown to possess the ability to successfully remove toxic U (VI) from the environment by either reduction (generally by bacteria) or biosorption (usually by fungi) (van Heerden et al., 2008).

Recently, the microbial reduction of metals has attracted interest as these transformations can play crucial roles in the cycling of both inorganic and organic species and therefore have opened up new and exciting areas of research with potential practical application (Anderson et al., 1998; Rooney-Varga et al., 1999; Lovley and Lloyd, 2000; Anderson et al., 2003; Lovley et al., 2004). Dissimilatory metal reducing bacteria (DMRB) have been shown to gain energy to support anaerobic growth by coupling the oxidation of $H_2$ or organic matter to the reduction of a variety of multivalent metals. This metabolism can lead to the complete mineralization of organic matter or to the precipitation and immobilization of metal contaminants under anaerobic conditions (Sani et al., 2002).

For the bioremediation of uranium contaminated sites, the chemistry of the element offers an approach that has received much attention in the last 20 years. The oxidation state of uranium is crucial to its stability, mobility and bioavailability. The oxidized or hexavalent, (VI), state of uranium is highly soluble and therefore mobile, while the reduced or tetravalent, (IV), state is relatively insoluble. In waste, uranium is present primarily as soluble salts of the uranyl ion ($UO_2^{2+}$). When the uranyl ion is reduced from the U (VI) oxidation state to a lower oxidation state such as U (IV), the solubility decreases and it becomes immobilized.

The list of bacteria known in the art to reduce U (VI) is growing. When *Thermus scotoductus* SA-01 is incubated anaerobically with U (VI), U (VI) will precipitate out of solution indicating that *Thermus scotoductus* SA-01 has the ability to reduce U (VI). Studies have also shown that *Thermus scotoductus* SA-01 has the ability to reduce almost 100% of a 0.25 mM U (VI) solution under anaerobic conditions with lactate as an electron donor in less than 30 hours (van Heerden et al., 2008).

However, very little is known about the mechanisms involved in U (VI) reduction and the proteins involved in these mechanisms and accordingly conclusive evidence as to which protein(s) are responsible for uranium reduction is still lacking.

For purposes of the present specification, "polypeptide" is understood as meaning peptides or proteins which comprise two or more amino acids bonded via peptide bonds.

SUMMARY OF THE INVENTION

According to a first aspect thereof, the present invention provides an isolated polypeptide derived from *Thermus scotoductus* strain SA-01 that is responsible for the reduction of uranium (VI), in a source of uranium (VI), to uranium (IV), wherein the polypeptide comprises the amino acid sequence of SEQ ID No: 1.

The isolated polypeptide is characterized in that it is a homogenous protein, having a molecular mass of 70 kDa, as shown by SDS-PAGE gel analysis.

The invention further provides for the isolated polypeptide to be a peptide ABC transporter, peptide-binding protein, as revealed by NCBI BLASTP analysis.

The Applicant believes that the isolated polypeptide identified herein is capable of performing more than one function, namely that of a peptide ABC transporter, peptide-binding protein and that of uranium reductase. Such proteins are commonly referred to in the art as "moonlighting proteins".

The isolated polypeptide identified herein possesses a disulphide bond, which when cleaved by a reducing agent, supplies a nucleation site for U (VI) reduction.

According to a second aspect thereof, the present invention provides isolated nucleic acid molecules coding for the amino acid sequence of SEQ ID No: 1 comprising a nucleotide sequence of SEQ ID No: 2.

For ease of reference, the amino acid sequence and nucleotide sequence referred to in this description and contained in the sequence listing filed herewith are also set out below. The underlined amino acids set forth in SEQ ID No: 1 represent the N-terminal amino acid sequence which was used to identify the polypeptide as a peptide ABC transporter, peptide-binding protein.

SEQ ID No: 1-
MetArgLysValGlyLysLeuAlaValPheGlyLeuAlaAlaLeuGlyLeuAlaLeuAla<u>GlyProGlnAspAsnSerLeuVal</u>

<u>IleGlyAlaSer</u>GlnGluProArgValLeuAlaGlyAspPheLeuSerIleIleSerAsnGlnSerIleLysLeuGluIleGlu

GlnTyrLeuPheAlaProLeuIleGlyPheAsnAlaAsnSerGluAsnPheProValLeuValThrGluValProThrArg

-continued

GlnAsnGlyArgLeuArgValThrAspIleGlyGlyGlyLysLysArgLeuGluMetAspLeuThrIleArgProAspAlaArg

TrpSerAspGlyLysProIleThrThrGluAspValAlaPheTyrTyrGluValGlyLysAlaLysGlyMetProValLeuAsn

ProAspTyrTrpGluArgValAsnLeuArgValArgAspAlaArgAsnPheThrValIlePheGluProAlaTyrTyrTyr

AspThrTyrGlyGlyThrTyrGlySerProIleGlyTyrAlaProLysHisIleMetGlyAlaGluTrpGluLysValLysAla

AlaAlaArgAsnLeuAspProAspLysAspAlaGluArgLeuAsnGluLeuTyrArgAsnPhePheLeuLysPheAlaThr

ProGlnAlaLeuAsnArgGlyAlaMetValTyrSerGlyAlaPheLysLeuArgArgTrpValProGlyAsnSerIleGluMet

GluArgAsnProAsnPheProIleLysProGluGlyGlyGluSerArgTyrValGlnArgValValTyrArgPheIleGlnAsn

ThrAsnSerLeuLeuValAlaValLeuGlyGlySerIleAspAlaThrSerSerValSerLeuThrPheAspGlnGlyArg

SerArgGlnLeuThrSerArgAlaProGlyArgPheAspIleTrpPheValProGlyAlaIleTrpGluHisIleAspValAsn

LysPheGluAsnCysGlnAlaValArgAspLeuGlyLeuAsnAspValArgThrArgArgAlaLeuLeuHisAlaLeuAsn

ArgGluGlyLeuValLysAlaPhePheAspGlyLeuGlnProValAlaHisThrTrpIleAlaProValAsnProLeuPheAsn

ProAsnValArgLysTyrGluPheAspLeuLysLysAlaGluAlaLeuLeuAlaGluMetGlyTrpArgLysGlyProAsp

GlyIleLeuGlnArgThrValGlyGlyArgThrValArgPheGluIleGluPheValThrThrAlaGlyAsnAlaIleArgGlu

ArgThrGlnGlnPhePheAlaGluAspLeuLysLysIleGlyIleAlaValLysIleAsnAsnAlaProSerAlaValValPhe

AlaAspAspTyrIleGlnArgAlaSerGluCysLysTrpThrGlyLeuPheGluPheAlaTrpValSerAsnLeuAlaGluAsp

GlySerLeuPheGlnTyrLysAsnLeuAsnThrGlyAlaIleMetValProThrLysGluAsnAsnTyrGlnGlyGlnAsnIle

GlyGlyTrpArgAsnAspGluPheAspArgLeuThrSerGlnGlyValLeuGluPheAspGluAlaArgArgLysGlnLeu

PheTrpArgAlaGlnGluIleTrpAlaGluGluLeuProAlaLeuProLeuTyrPheArgAlaAsnProTyrValValArg

LysGlyLeuValAsnTyrValAlaSerAlaTyrAlaGlyGlyTyrGlyTyrProGlyTrpAsnAlaTrpGluIleGlyTrpGlu

SerArgGlyAlaValLysLysTrpAspGlnAlaLysTyrAlaLeuSerValLys

SEQ ID No: 2-

ATGAGAAAAGTAGGCAAGCTGGCTGTATTCGGTTTAGCCGCCCTGGGCTTGGCCCTGGCG

GGGCCCCAGGACAACAGCCTGGTCATAGGGGCTTCGCAGGAGCCCCGGGTTCTGCGGG

GGACTTCCTAAGCATCATCTCCAACCAGTCCATCAAGTTGGAGATCGAGCAGTACCTCTTC

GCCCCCCTCATCGGTTTCAACGCCAACAGCGAAAACTTTCCCGTGCTGGTCACCGAGGTG

CCCACCCGGCAAAACGGGCGTTTGCGGGTGACGGACATCGGCGGGGGCAAGAAGCGCTTG

GAGATGGACCTCACCATCCGGCCCGATGCCCGCTGGTCCGACGGCAAGCCCATCACCACC

GAGGATGTGGCCTTCTACTACGAGGTGGGCAAGGCCAAGGGGATGCCGGTGCTCAACCCG

GACTACTGGGAGCGGGTGAACCTCCGGGTCAGGGACGCCCGCAACTTCACCGTGATCTTT

GAGCCCGCCTACTACTACGACACCTACGGCGGCACCTACGGCTCCCCCATCGGCTACGCT

CCCAAGCACATCATGGGCGCCGAGTGGGAGAAGGTGAAAGCGGCGGCCCGGAACCTGGAT

CCCGATAAGGATGCGGAGAGGCTCAACGAGCTCTACCGCAACTTCTTCCTCAAGTTCGCC

ACTCCCCAGGCCCTAAACCGGGGAGCCATGGTCTACTCGGGGGCCTTCAAGCTGCGGCGC

TGGGTGCCGGGGAACTCCATTGAGATGGAGCGGAACCCCAACTTCCCCATCAAGCCCGAG

GGTGGGGAGAGCCGGTACGTGCAGAGGGTGGTCTACCGCTTCATCCAGAACACCAACTCC

CTCCTGGTGGCCGTCCTGGGCGGGAGCATTGACGCCACCTCCAGCGTCTCCCTCACCTTT

GACCAAGGCCGTAGCCGCCAGCTCACCTCCCGGGCCCCTGGCCGCTTTGACATCTGGTTC

GTGCCCGGGGCCATCTGGGAGCACATTGACGTCAACAAGTTTGAGAACTGCCAGGCGGTC

CGCGACTTGGGCCTGAACGACGTCCGCACCCGTCGGGCCCTCCTCCACGCTCTGAACCGC

GAGGGGTTGGTCAAGGCCTTCTTTGACGGCCTCCAGCCCGTGGCCCACACCTGGATCGCC

CCCGTCAACCCCCTCTTCAACCCCAATGTGCGGAAGTACGAGTTTGACCTGAAGAAGGCG

-continued

```
GAGGCGCTCTTGGCGGAGATGGGCTGGAGGAAGGGGCCGGACGGCATCCTTCAGCGCAC

CGTGGGTGGCCGCACCGTGCGCTTTGAGATTGAGTTCGTCACCACCGCGGGCAACGCTATC

CGGGAGCGCACCCAGCAGTTCTTCGCCGAGGACCTGAAGAAGATCGGCATCGCCGTCAAG

ATCAATAACGCCCCAGCGCCGTGGTCTTCGCCGACGACTACATCCAGCGGGCCAGCGAG

TGCAAGTGGACCGGGCTGTTTGAGTTCGCTTGGGTTTCCAACCTGGCCGAGGATGGCTCC

CTCTTCCAGTACAAGAACCTGAACACCGGGGCCATCATGGTGCCCACCAAGGAGAACAAC

TACCAGGGGCAGAACATCGGCGGCTGGCGCAACGACGAGTTTGACCGTCTGACGAGCCAG

GGTGTCCTGGAGTTTGACGAGGCCAGGCGGAAGCAGCTCTTCTGGAGGGCCCAGGAGATC

TGGGCCGAGGAGCTGCCTGCCTTGCCCCTCTACTTCCGCGCTAACCCCTACGTGGTGCGG

AAGGGCCTGGTCAACTACGTGGCCAGCGCTTACGCGGGCGGCTACGGTTACCCCGGCTGG

AACGCTTGGGAGATCGGCTGGGAGAGCCGCGGCGCCGTGAAGAAGTGGGACCAGGCGAA

GTACGCTCTTTCCGTCAAGTAA
```

In an embodiment of the invention, the polypeptide indentified herein is isolated from a culture of *Thermus scotoductus* strain SA-01, recovered and purified. Exemplary procedures suitable for such recovery and purification include column chromatographic methods and size exclusion techniques of the type known and described in the art. In an embodiment thereof, the present invention provides for purification of the protein to be achieved by nickel affinity column chromatography followed by gel filtration. In an alternative embodiment thereof, the present invention provides for the protein to be purified by heat denaturation followed by gel filtration.

In an alternative embodiment, the polypeptide of SEQ ID No: 1 is produced recombinantly by expressing the nucleotide sequence of SEQ ID No: 2 encoding the polypeptide in a host cell. With the aid of an expression vector, the nucleic acid molecules containing the nucleotide sequences of SEQ ID No: 2 may be transfected and expressed in a host cell.

Thus the present invention also relates to vectors that include the nucleotide sequence of SEQ ID No: 2, host cells that are genetically engineered with one or more recombinant expression vectors, and the production of the polypeptide of SEQ ID No: 1 as indentified herein by recombinant techniques as is well known in the art.

The present invention further provides a method for producing at least one polypeptide, as indentified herein, that is responsible for the reduction of uranium (VI), in a source of uranium (VI), to uranium (IV), the method including the steps of:
a) transfecting the nucleic acid molecules of SEQ ID NO: 2 into a host cell;
b) culturing the host cell so as to express the polypeptide of SEQ ID NO: 1 in the host cell; and
c) optionally, isolating and purifying the polypeptide of SEQ ID NO: 1.

Also according to the invention, there is provided a microorganism transformed with a U (VI) resistant gene obtained from the host cell described above, or any U (VI) resistant functional part thereof.

For purposes of the present invention, uranium reductase activity is determined by measuring a decrease in hexavalent uranium. Uranium reductase activity is measured spectrophotometrically using 2-(5-bromo-2-pyrdulazo)-5-diethylaminophenol.

According to a third aspect thereof, the present invention provides a process for the bioremediation, or at least partial bioremediation, of a site contaminated with a source of U (VI), the process comprising the steps of introducing an electron donor to the contaminated site in order to stimulate the proliferation of *Thermus scotoductus* strain SA-01 to reduce the U (VI) in the source of U (VI) present therein, to U (IV), or the step of removing environmental media from a U (VI) contaminated site and introducing an electron donor to such environmental media for a sufficient period of time so as to allow *Thermus scotoductus* strain SA-01 to reduce U (VI), in the source of U (VI) present therein, to U (IV).

In an embodiment of the instant invention, *Thermos scotoductus* strain SA-01 is derived from the Mponeng mine located on the north-western rim of the Witwatersrand Basin in the North West Province of South Africa which mine is operated by Western Deep Levels, Inc., or from environmental media obtained from this site.

For purposes of the present specification, the term "environmental media" denotes solid and liquid wastes, soils, sediments, water bodies, or a combination of one or more thereof.

In an embodiment of the present invention, the source of U (VI) is selected from the group consisting of $UO_2(CH_3COO)_2.2H_2O$ and $UO_2(NO_3)_2$. It will be appreciated that the source of uranium of the present invention is not limited to the foregoing and accordingly may be any suitable source of hexavalent uranium.

In one embodiment of the present invention, reduction takes place under aerobic and/or anaerobic conditions. Preferably, reduction takes place under anaerobic conditions so as to prevent the reduced U (IV) from being oxidized to U (VI).

As mentioned herein before, the reduction of U (VI) to U (IV) is initiated by an electron donor. It will be appreciated that the electron donor may be any suitable electron donor of the type known and described in the art. In one embodiment of the invention, the electron donor is selected from the group consisting of $H_2$, reduced quinone (in particular hydroquinone), acetate, lactate, citric acid, and pyruvate.

The aforesaid process can be employed for the bioremediation, or at least partial bioremediation, of a site contaminated with a source of hexavalent U that can be practiced in situ, ex situ, or both.

According to a fourth aspect thereof, the present invention provides for the use of an isolated polypeptide of SEQ ID No: 1, as identified and characterized herein, in the reduction of uranium (VI), in a source of uranium (VI), to uranium (IV).

Furthermore, the present invention provides for the use of *Thermos scotoductus* strain SA-01 in the bioremediation, or at least partial bioremediation, of a U (VI) contaminated site or of U (VI) contaminated environmental media.

The invention provides further for the use of *Thermos scotoductus* strain SA-01 in the bioremediation, or at least partial bioremediation, of a U (VI) contaminated site or of U (VI) contaminated environmental media, wherein said *Thermus scotoductus* strain SA-01 is derived from the U (VI) contaminated site or the U (VI) contaminated environmental media that is to be remediated, or at least partially remediated.

Also according to the invention, there is provided the use of a microorganism transformed with a U (VI) resistant gene obtained from the host cell described above, or any U (VI) resistant functional part thereof, in the bioremediation, or at least partial bioremediation, of a U (VI) contaminated site or of U (VI) contaminated environmental media.

These and other objects, features and advantages of the invention will become apparent to those skilled in the art following the detailed description of the invention.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

EXAMPLES

The invention was performed in accordance with the following steps.

Growth of *Thermus scotoductus* SA-01

The thermophilic bacterium, *Thermus scotoductus* strain SA-01, employed herein, was isolated in 1999 by Kieft et al. from groundwater sampled at a depth of approximately 3.2 km in the Mponeng gold mine which is located on the northwestern rim of the Witwatersrand Basin in the North West Province of South Africa operated by Western Deep Levels, Inc.

*Thermus scotoductus* SA-01, deposited under ATCC Accession No. 700910; American Type Culture Collection, was plated out from a glycerol stock on solid TYG medium and allowed to grow for 24 hours at 65° C. This was then replated again on solid TYG medium and allowed to grow for 24 hours at 65° C. A pre-inocculum was then prepared by inoculating a loop of growth from the plate in 50 ml of liquid TYG medium. This was grown for 8 hours at 65° C. after which 10 ml of growth was transferred to 90 ml of liquid TYG medium. This was then grown for 8 hours at 65° C. after which 5 ml of growth was transferred to 95 ml of liquid TYG medium.

8 hours was determined beforehand to be the time needed for the organism to grow to the late exponential phase.

Figure 1:
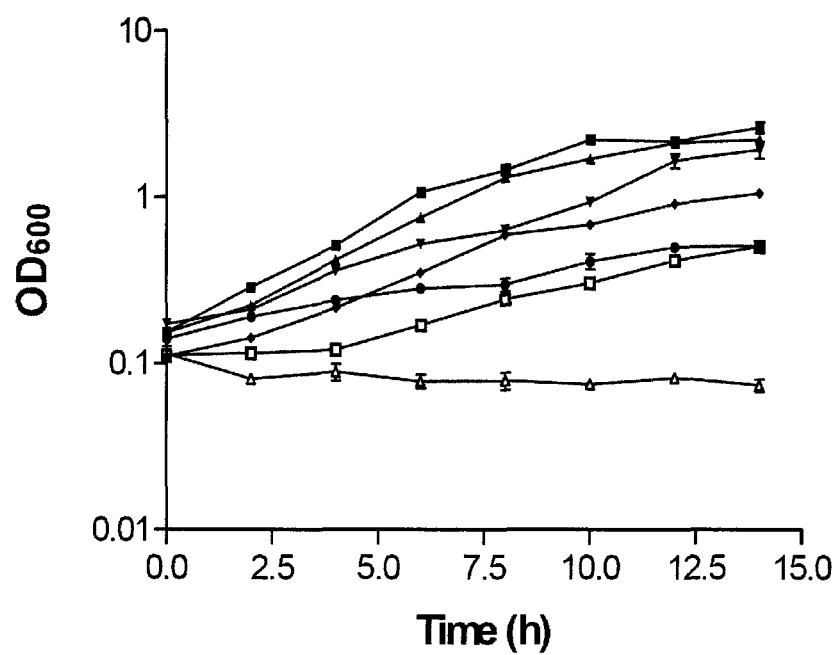
FIG. 1: is a graph depicting growth curves for *Thermus scotoductus* in different concentrations of uranium. TYG medium (■) amended with 0.25 mM (▲), 0.5 mM (▼), 0.75 mM (◆), 1.0 mM (●), 1.25 mM (□) and 1.5 mM (Δ) U(VI) during inoculation (t=0)

As can be seen from FIG. 1, *Thermus scotoductus* SA-01 has the ability to grow in uranium concentrations of up to 1.25 mM. However, as can further be seen from said Figure, an increase in the concentration of uranium above 1.25 mM leads to a decrease in the ability of *Thermus scotoductus* SA-01 to grow effectively.

Spectrophotometric Determination of U (VI)

All reagents were of analytical reagent grade. Deionized distilled water was used for the preparation of standard solutions. 100 mM was prepared by dissolving $UO_2(CH_3COO)_2 \cdot 2H_2O$ in water. The prepared solution was stored in the dark and used for sequential dilution. 5-Br-PADAP was used to prepare a 0.05% solution by dissolving the reagent in ethanol. The complexing ligand solution (pH 7.8) was prepared by dissolving 1 g of NaF and 13 g of sulphosalicyclic acid in 40 ml water, the pH was then adjusted with NaOH and the solution was diluted to 100 ml. The buffer solution (pH 7.8) was prepared by diluting 14 g of TEA in 80 ml of water, the pH was then adjusted with perchloric acid, and the solution was left to stand overnight. Before use, the pH of the buffer solution was adjusted to 7.8 with perchloric acid and the solution diluted to 100 ml. All optical density measurements were made on a Spectronic® Genesys™ 5 at 600 nm (Johnson and Florence, 1971).

U (VI) dilutions were made by diluting the stock solution with water. 100 μl of the U (VI) dilution was taken in a 1.5 ml eppendorf tube containing 25 μl of complexing solution. To the above, the 100 μl of the buffer solution and 80 μl of Br-PADAP solution was added and made up with 620 μl ethanol and 75 µl water. This coloured solution was allowed to stand for about 2 h and absorbance was measured at 578 nm against a reagent blank (Johnson and Florence, 1971).

Figure 2:
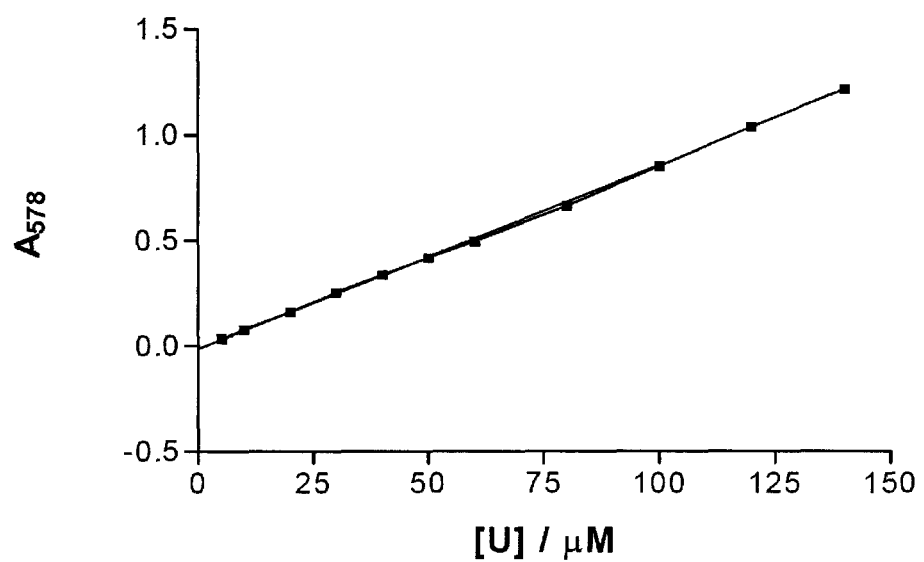
FIG. 2: is a graph depicting a standard curve of the optical density reading of the specific diluted uranium sample vs the known U (VI) concentration for the specific diluted uranium sample.

A standard curve was constructed, as depicted in FIG. 2, by plotting the optical density reading of the specific diluted sample vs the known U (VI) concentration for the specific diluted sample.

U (Vi) Reduction by *Thermus scotoductus* SA-01 Under Non-Growth Conditions

*T. scotoductus* SA-01 cells were harvested from growth standardized inoculum. The cells were washed three times with 20 mM Tris-HCl buffer, pH 7.0, and the cell suspension purged with $O_2$-free $N_2$. To initiate the assay, a sample of the culture was added to a tube containing the assay solution (uranyl acetate in Tris-HCl buffer, pH 7.0, plus Na lactate as electron donor) to a final concentration of 0.25 mM U (VI) and 10 mM electron donor and subjected to analysis as described below. This was all done in an anaerobic chamber to prevent reduced U (IV) from being oxidized to U (VI). Along with the cell-free control, an electron donor free control was also prepared.

Uranium reductase activity was determined by measuring the decrease of hexavalent uranium. U (VI) was analyzed spectrophotometrically using 2-(5-bromo-2-pyrdulazo)-5-diethylaminophenol (Johnson and Florence, 1971).

Figure 3:
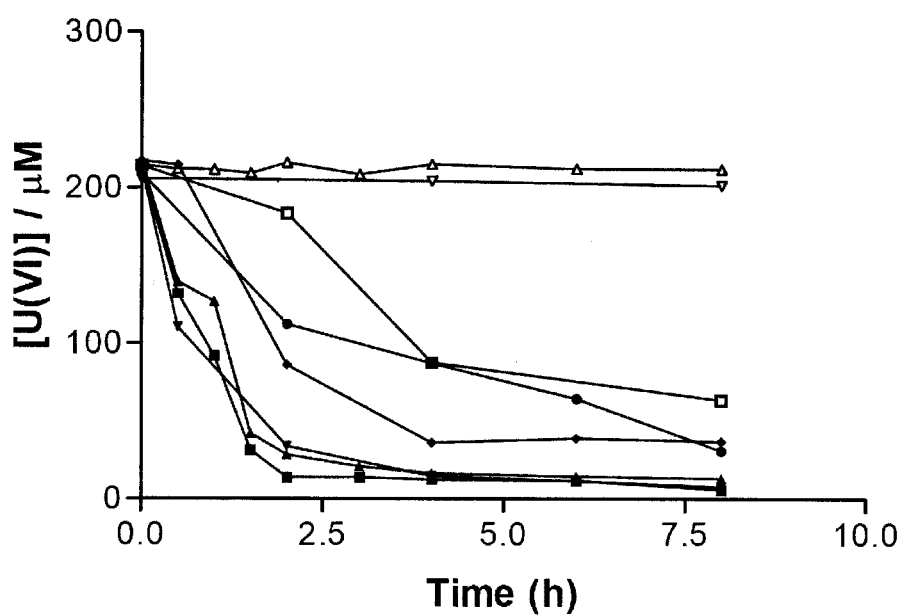
FIG. 3: is a graph showing the reduction of uranium (VI) by *T. scotoductus* SA-01 under non-growth conditions. Cells harvested in late exponential phase with assay solution containing 0.25 mM U(VI) and 10 mM lactate as electron donor (■), control assay solution of cells harvested in late exponential phase containing 0.25 mM U(VI) and no electron donor (▲), cells harvested in early exponential phase with assay solution containing 0.25 mM U(VI) and 10 mM lactate as electron donor (▼), control assay solution of cells harvested in early exponential phase containing 0.25 mM U(VI) and no electron donor (◆), cells harvested in late exponential phase with assay solution containing 0.25 mM U(VI) and 10% hydrogen as electron donor (●), control assay solution with autoclaved cells with no electron donor (□), control assay solution lacking cells with 10 mM lactate (Δ) and 10% hydrogen (∇) as electron donors.

When *Thermus* SA-01 is incubated anaerobically with U (VI), U (IV) will precipitate out of solution as indicated by a black precipitate (Haas and Northop, 2004) formed in the cell pellet. Most of the uranium (VI) was transformed to U (IV) in under 20 hours, as can be seen in FIG. 3, which coincides with what was previously described in literature (Kieft et al., 1999).

It was observed that even without an electron donor, the cells were still able to reduce the hexavalent uranium. No chemical reduction was observed in the cellfree control indicating that the reduction has to be due to cellular activity.

After the experiment was completed, the cells used were exposed to oxygen overnight which led to the disappearance of the black precipitate. Uranium (VI) determination was also done after the exposure to air and it was found that most of the U (IV) in the sample was oxidized to U (VI). This indicates that the reduction of U (VI) to U (IV) occurred since if uranium complexes, for instance U (VI) phosphate-type complexes, were formed by bioprecipitation or bioaccumulation, it would not have resulted in the reappearance of U (VI) under aerobic conditions.

Uranium (VI) Reduction with Different Electron Donors

To determine the most effective electron donor for whole cell uranium (VI) reduction, various reduction assays were performed with electron donors determined to be most relevant. In this regard, $H_2$, reduced quinone (particularly hydroquinone), acetate, lactate, citric acid, and pyruvate were employed. It was observed that whilst each electron donor is capable of producing a set amount of reducing equivalents (some electron donors more than others), uranium (VI) reduction is not directly coupled to the produced reducing equivalents. Accordingly, it can be concluded that the specific electron donor does not have any significant effect on uranium (VI) reduction.

Uranium (VI) Reduction at Different pH and Temperature Values

Whole cell uranium (VI) reduction under non-growth conditions was performed over a pH range of 5 to 9. The whole cell uranium (VI) reduction activity seemed to prefer a more neutral pH with maximum activity being observed at a pH of between 7 and 8. Very low reaction rates were observed at pH values below 7. Since all appropriate controls were evaluated, this might be due to the fact that the assay does not function in this pH region.

The optimum temperature for whole cell uranium (VI) reduction was determined over a range of 35° C. to 75° C. It was observed that temperature did not seem to have any significant effect on whole cell reduction.

Preparation of Subcellular Fractions

Subcellular fractions were prepared as described by Kaufmann and Lovley (2001). *T. scotoductus* SA-01 cells were harvested from growth standardized inoculum at 8 h of growth and washed three times with 50 mM Tris-HCl buffer, pH 7.8. Cells were then resuspended in 50 mM Tris-HCl buffer, pH 7.8, containing 25% (w/v) sucrose. To accomplish cell wall lysis, lysozyme (20 mg) was added to the cell suspension (approximately 1 g wet weight) and stirred for 20 min at 37° C. $Na_2$-EDTA was added to a final concentration of 5 mM and stirred for another 15 min at 37° C. Finally $MgCl_2$ was added to a final concentration of 13 mM and the suspension was stirred for 15 min at 37° C. Separation of the spheroplast from the periplasmic fractions was obtained by centrifugation (20 000×g, 30 min). Spheroplasts were resuspended in 50 mM Tris-HCl buffer, pH 7.8.

To obtain the membrane and cytoplasmic fraction, the protocol as described by Gaspard et al., (1998), was used. DNAse and RNAse was added to final concentrations of 5 µg/ml and 10 µg/ml respectively as well as protease inhibitors and the cells were broken by ultrasonic treatment (3 times, 75 W, 5 min) with a sonifier (Branson Sonic Power Cell Disruptor B-30) in an ice-water bath. The suspension was then centrifuged (4000×g, 10 min) at 4° C. to remove cellular debris. To separate the membrane fraction from the cytoplasmic fraction, the supernatant was centrifuged (100 000×g, 90 min). The pellet was resuspended in 50 mM Tris-HCl buffer, pH 7.8.

The membrane, periplasmic and cytoplasmic fractions were all dialysed against 20 mM MOPS buffer, pH 7.0, with Snakeskin®Pleated Dialysis Tubing (10 000 MWCO) at 4° C. with 3×2 L buffer changes.

Determination of U (VI) Reduction Activity in Subcellar Fractions

With $H_2$ and Reduced Quinones as Electron Donors

The periplasmic and membrane fractions were subjected to uranium (VI) reduction experimentation as described above with the exception that the fractions were purged with $O_2$-free $N_2/H_2/CO_2$ (90%/10%/10%) mixed gas and supplemented with 2 mM hydroquinone to introduce 10% $H_2$ and reduced quinones as electron donors. To initiate the assay, uranyl acetate was added to a sample of the fraction to a final concentration of 0.25 mM U (VI) and subjected to analysis. This was all done in an anaerobic chamber to prevent reduced U (IV) from being oxidized to U (VI).

The combination of the periplasm and membrane fractions was screened for U (VI) reduction activity, since this combination has shown the most promise pertaining to the presence of the uranium reductase. Hydroquinone and $H_2$ were utilized as electron donors as these are the electron donors preferred from literature for this type of protein.

Figure 4:
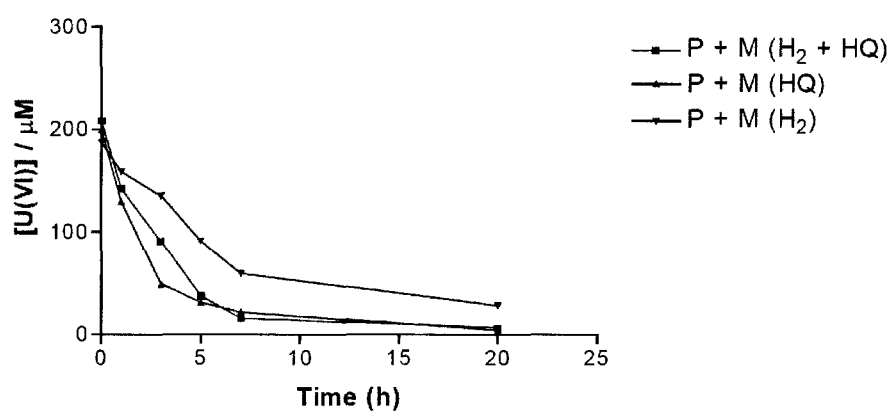
FIG. 4: is a graph depicting uranium (VI) reduction activity of the combination of the membrane and periplasmic fractions from *T. scotoductus* SA-01 after dialysis and being purged with 10% $H_2$ gas and hydroquinone as electron donors.

A graph was then constructed, as shown in FIG. 4, depicting uranium (VI) reduction activity of the combination of the membrane and periplasmic fractions from *T. scotoductus* SA-01, after dialysis and being purged with 10% $H_2$ gas and hydroquinone as electron donors.

As can be seen from FIG. 4, a combination of the $H_2$ and reduced quinones delivered the best reduction activity. Furthermore, a blackish-yellow precipitate was formed. Since it has been shown that proteins in the periplasm precipitates out a yellow U (VI) precipitate, it is no surprise that the formed precipitate was not completely black.

Optimization of the Method for the Isolation of the Protein of Interest by Chromatographic Methods Extraction of Ionically Bound Membrane Proteins The membrane pellet was resuspended in 20 mM MOPS buffer, pH 7.0, by stirring overnight at 5° C. The volume of the membrane fraction was doubled with 1 M KCl in 20 mM MOPS buffer, pH 7.0. The solution was then stirred for 2 h at room temperature to extract the peripheral membrane proteins and the resulting suspension was ultra-centrifuged at 100 000×g for 90 min at 4° C. to pellet the membrane. The KCl extractable membrane fraction (the supernatant from the centrifugation step) was dialyzed against a 20 mM MOPS buffer pH 7.0 at 5° C. with 3×2 L buffer changes.

Isolation of the Membrane/Periplasmic Fractions

The dialyzed KCl extracted membrane fraction in combination with the periplasmic fraction was applied to a Super-Q Toyopearl (8 cm×2.8 cm) column previously equilibrated with 20 mM MOPS buffer, pH 7.0. The columns were washed with 20 mM MOPS buffer, pH 7.0, until the $A_{280\,nm}$ readings were less than 0.01. A salt gradient of 0-1.0 M NaCl at a flow rate of 5 ml/min was used to elute proteins.

Fractions determined to be active for uranium (VI) reduction activity were pooled and dialyzed against 20 mM MOPS buffer, pH 7.0, with Snakeskin®Pleated Dialysis Tubing (10 000 MWCO) at 4° C.

Figure 5:
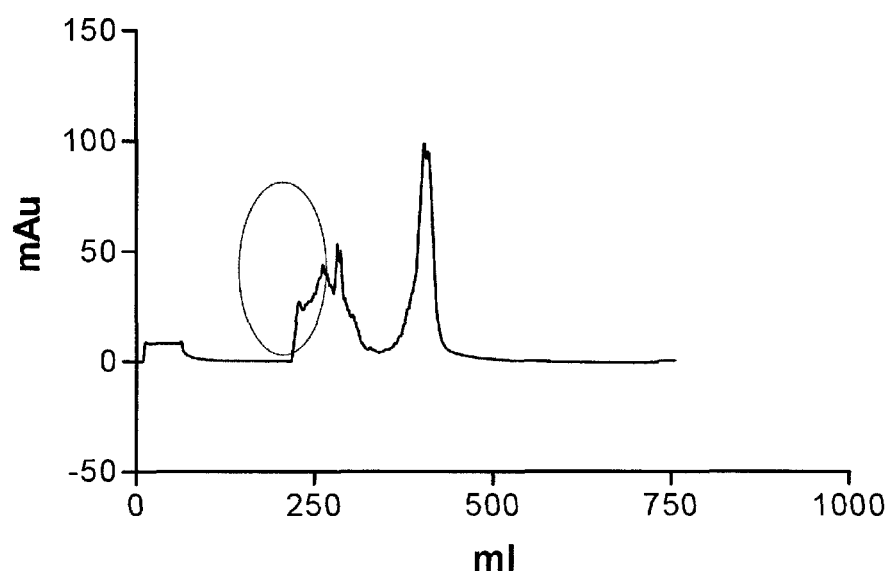
FIG. 5: is a graph depicting an elusion profile for Super-Q Toyopearl pertaining to uranium (VI) reduction activity.

A graph depicting the elusion profile for the Super-Q Toyopearl was then constructed, as shown in FIG. 5. The circled peaks in said Figure indicate the produced uranium (VI) reduction activity. The circled peaks were pooled and applied to the SP Toyopearl after dialysis.

The dialysate was applied to a SP Toyopearl (8 cm×2.8 cm) column previously equilibrated with 20 mM MOPS buffer, pH 7.0. The column was washed with 20 mM MOPS buffer, pH 7.0, until the $A_{280\,nm}$ readings were less than 0.01. A salt gradient of 0-1.0 M NaCl at a flow rate of 5 ml/min was used to elute proteins. Selected fractions were collected (10 ml) and tested for uranium (VI) reduction activity.

Figure 6:
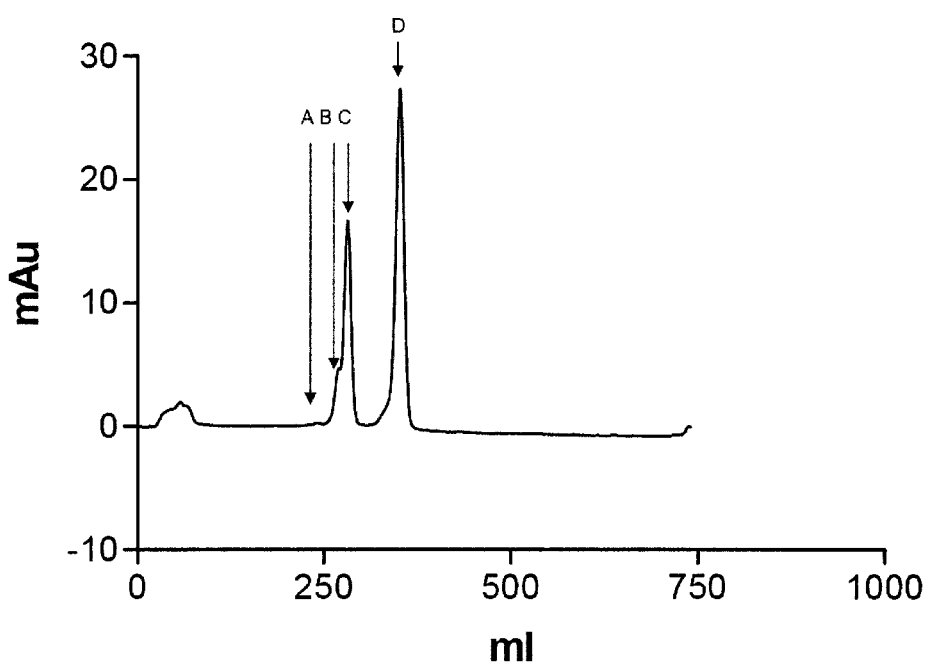
FIG. 6: is a graph depicting an elusion profile for SP Toyopearl pertaining to uranium (VI) reduction activity.

A graph depicting the elusion profile for the SP Toyopearl was thereafter constructed, as shown in FIG. 6. Arrow A represents fraction 11, arrow B represents fraction 16, arrow C represents fraction 19, and arrow D represents fraction 33. From this Figure, it can be seen that fractions 16, 19 and 33 indicate uranium (VI) reduction activity.

Figure 7:
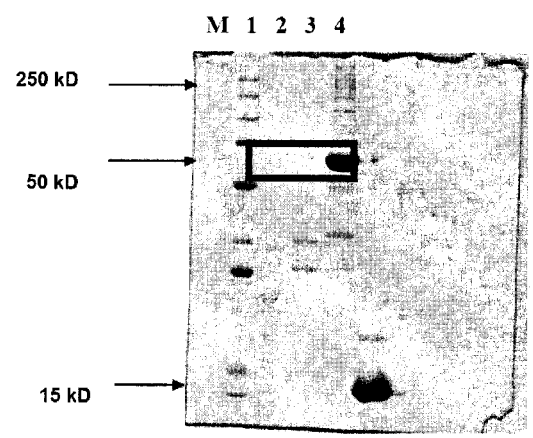
FIG. 7: is a SDS-PAGE gel analysis depicting the isolated uranium reductase protein.

SDS-PAGE gel analysis was done on the selected fractions from chromatographic separation on the SP Toyopearl resin. As shown in FIG. 7, lane M represents the molecular mass marker proteins; lane 1 represents fraction 11; lane 2 represents fraction 16; lane 3 represents fraction 19; whilst lane 4 represents fraction 33. Accordingly, the resulting SDS-PAGE gel analysis indicated that the only protein present in all three of these fractions was the +/−70 kDa protein.

Sequence Determination of Unknown Protein

N-Terminal Sequencing

Fraction 19 was loaded onto a 10% SDS PAGE gel and run at 100V. After the run was completed the gel was blotted onto a PVDF membrane according to the manufacturer's specification. The blotted membrane was then stained with Coomassie Brilliant Blue and the band of interest was cut out and sent for sequencing.

The results obtained revealed that the N terminal sequence is XPXDNSLVIG

BLASTP analysis in the NCBI web using the "DNSLVIG" sequence resulted in 100% identity with the following:
  (i) a dipeptide-binding protein from *Thermus thermophilus* HB27;
  (ii) an extracellular solute-binding protein family 5 (ABC-type dipeptide transport protein) from *T. aquaticus* Y51 MC23; and
  (iii) an oligopeptide binding protein from *T. thermophilus* Hhb8.

All of these proteins were identical in sequence.

The sequences from the proteins obtained from NCBI BLASTP analysis were blasted against the *Thermus scotoductus* SA-01 draft genome and resulted in 100% identity with a peptide ABC transporter protein, peptide binding protein. Also a BLASTP analysis of the N terminal sequence against the draft genome sequence of *Thermus scotoductus* SA-01 resulted in 100% identity with a peptide ABC transporter, peptide-binding protein.

Therefore, XPXDNSLVIG represents the first residues of the mature sequence of the protein. After the BLASTP analysis, it can be deduced from the chromatogram of the N-terminal sequencing that the first amino acid corresponds to G and the third residue corresponds to Q.

In view of the foregoing, it was deduced that the N-terminal sequence is GPQDNSLVIG From the aforesaid, it can be concluded that the protein involved in uranium reduction is the peptide ABC transporter, peptide-binding protein. It can also be concluded that said protein moonlights as uranium reductase.

MS/MS Sequencing

Fraction 19 was loaded onto a 10% SDS PAGE gel and run at 100 V. After the run was completed, the gel band for the +/−70 kDa protein was cut out and freeze dried. The freeze dried sample was then sent to the Centre for Proteomic and Genomic Research in Cape Town for MS/MS analysis. A total of nine tryptic digested fragment spectra were obtained which was analyzed using the Mascot Distiller software.

Four of the spectra could then be also annotated to the peptide ABC transporter, peptide-binding protein.

The aforegoing therefore serves to verify that the protein in question is the peptide ABC transporter, peptide-binding protein.

Protein Expression and Purification

Vectors pET28, containing the sequence for the peptide ABC transporter, peptide-binding protein were constructed using methods known in the art. pET28 contains the sequence for attaching a histidine rich area to the N-terminus of the protein, thus enabling the protein to be purified with a nickel affinity column.

ABC/pET28 was then transformed into Rosetta-Gami 2(DE3)pLysS competent cells and inoculated into a LB medium containing an antibiotic, KAN for pET28. The cells were then cultured and grown to an OD of between 0.8-1.0 and protein expression was induced with the addition of 1 mM (final concentration) IPTG.

Four hours after induction, the cells were harvested and washed. The cells were broken by passage through a French pressure cell and the cytoplasmic fraction was harvested by ultracentrifugation (100 000×g, 4° C., 90'). The resultant protein from pET28 was then purified by a nickel affinity column followed by a gel filtration step.

Characterization of the Recombinant ABC Proteins

The recombinant protein was evaluated for the ability to reduce uranium (VI). The recombinant protein was characterized using the same physio-chemical parameters as used for characterizing the whole cells.

In order to demonstrate that the disulphide bond, present in the protein, provides a nucleation site for U (VI) reduction, a reducing agent needed to be applied in order to reduce the thiol moeity. Out of the possible reducing agents, namely dithiothreitol, sodium dithionite and β-mercaptoethanol that were assayed with uranium (VI), β-mercaptoethanol produced the lowest level of chemical reduction of uranium (VI).

An excess of β-mercaptoethanol was thus utilized to reduce the disulfide bond present in the protein before experimentation.

Generation of Cysteine Mutants of the Peptide ABC Transporter, Peptide-Binding Protein A homology model of the ABC transporter peptide-binding protein of *T. scotoductus* SA-01 was compiled using Yasara Structure & Whatif. The template used was the oligopeptide-binding protein of *T. thermophilus* HB8 (2D5W-B) which has a 90% identity (95% similarity) with the ABC transporter, peptide-binding protein of *T. scotoductus* SA-01.

Modelling of the protein revealed a disulphide bond which is present on the exterior of the protein, thereby supplying a possible nucleation site for U (VI) reduction once the bond has been reduced by the addition of a reducing agent such as β-mercaptoethanol.

The cysteine residues responsible for this bond are located at positions 337 and 481. Therefore, to probe the role of the cysteine residues in U (VI) reduction, the cysteine residues were each mutated to alanines by site-directed mutagenesis. A combination of both the two cysteine mutants was also devised.

The mutant proteins were thereafter purified using Ni-NTA affinity chromatography and were found to have greater than 98% purity on Coomassie-stained gels.

Other proteins with cysteine thiol-disulfide bridges have shown the ability to reduce U (VI), such as a thioredoxin from *Desulfovibrio desulfuricans* strain G20 (Li and Krumholtz, 2009).

U (VI) reduction by the cysteine mutants was thereafter performed in reactions containing 320 µg/ml of protein at pH 7 and 65° C.

Participation of the Cysteine Residues in Enzymatic Activity

Both the Cys-337 and Cys-481 mutants showed very little or negligible activity when compared to the wild-type. Also, the double mutant showed no significant activity. The results of these assays clearly indicate that Cys-337 and Cys-481 are required for U (VI) reduction.

The Effect of pH on Uranium (VI) Reduction

In essence, reduction performed with a reduced disulfide bond can be seen as reduction by hydrogen sulphide. Hua and coworkers (2006) observed that the reduction of uranium (VI) by hydrogen sulphide happened optimally at neutral pH values and could best be represented by the following equation:

$$UO_2^{2+}+HS^-=UO_2+S^0+H^+ \quad \text{(Hua et al., 2006)}$$

Figure 8:
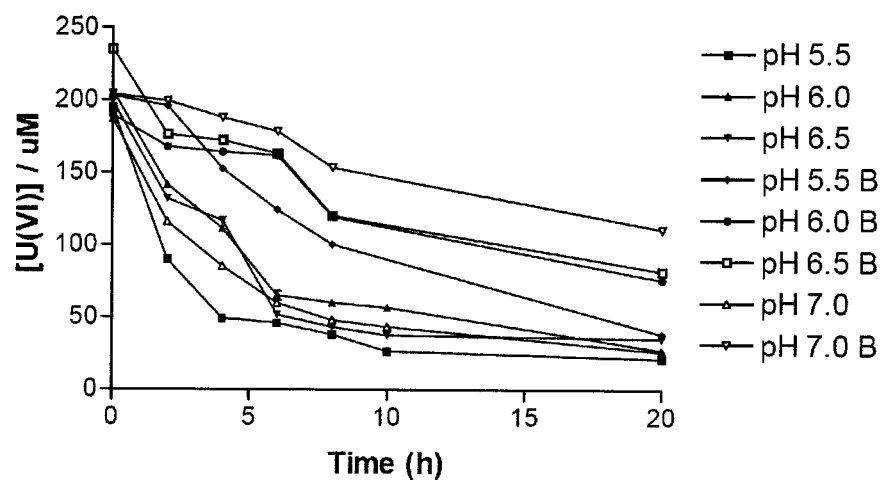
FIG. 8: is a graph depicting the reduction of uranium (VI) at different pH values. pH values (■) 5.5, (▲) 6.0, (▼) 6.5, (Δ) pH 7.0, (◆) 5.5 protein free control, (●) pH 6.0 protein free control, (□) pH 6.5 protein free control, (∇) pH 7.0 protein free control.
Figure 9:
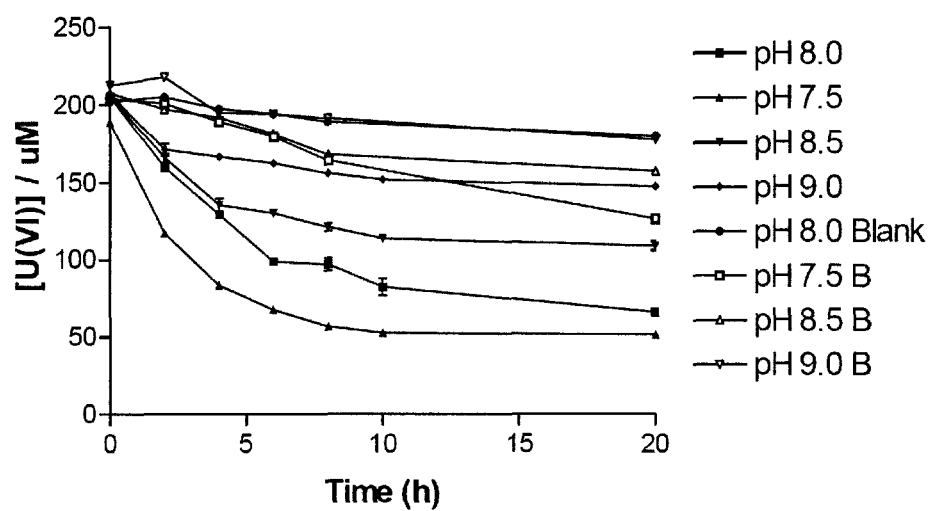
FIG. 9: is a graph depicting the reduction of uranium (VI) at different pH values. pH values (▲) 7.5, (■) 8.0, (▼) 8.5, (□) 9.0, (◻) pH 7.5 protein free control, (●) pH 8.0 protein free control, (Δ) pH 8.5 protein free control, (∇) pH 9.0 protein free control.

The highest rate of reduction can be observed for pH values between 7 and 8 (FIGS. 8 and 9), which coincides with what was observed in literature for sulphide reduction (Hua et al., 2006). At pH values below 7 and above 8, the rate of chemical reduction of uranium (VI) by β-mercaptoethanol in the samples lacking protein are very high. This might be due to pH inhibition of the reduction of the disulphide bond, producing increasing amounts of β-mercaptoethanol which are free to reduce the uranium (VI).

The Effect of Temperature on Uranium (VI) Reduction

Figure 10:
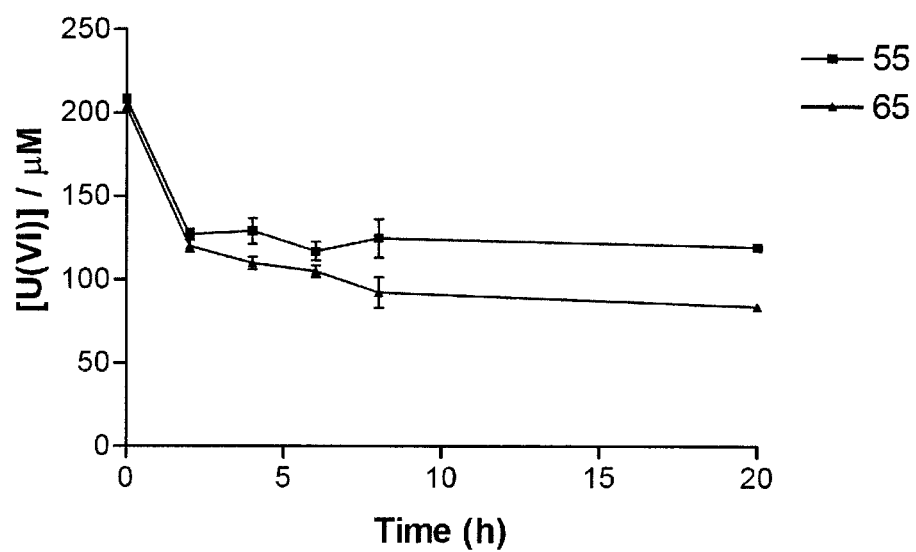
FIG. 10: is a graph depicting the reduction of uranium (VI) at 55° C. (■) and 65° C. (▲) with the blank rate subtracted.

The highest rate of reduction can be observed for temperature values between 55° C. and 65° C. (FIG. 10), coinciding with the optimal growth temperature for the organism (Kieft et al., 1999). At temperatures below 45° C., almost no activity was observed and above 65° C. the rates of chemical reduction of uranium (VI) by β-mercaptoethanol in the samples lacking protein were very high.

REFERENCES

Nies, D. H., and Silver, S. (1995) Ion efflux systems involved in bacterial metal resistances. *Journal of Industrial Microbiology* 14: 186-199.

Lovley, D. R., Phillips, E. J. P., Gorby, Y. A. and Landa, E. R. (1991) Microbial reduction of uranium. *Nature*. 350:413-416.

Anderson, R. T., Fleisher, M. Q. and LeHuray, A. P. (1998) Concentration, oxidation state, and particulate flux of uranium in the Black sea. *Geochimica et Cosmochimica Acta*. 53: 2215-2224.

Rooney-Varga, J., Anderson, R. T., Fraga, J. L., Ringleberg, D. and Lovley, D. R. (1999) Microbial communities associated with anaerobic benzene degradation in a petroleum-contaminated aquifer. *Applied and Environmental Microbiology*. 65:3056-3063.

Lovley, D. R., Holmes, D. E. and Nevin, K. P. (2004) Dissimilatory Fe(III) and Mn(IV) reduction. *Advances in Microbial Physiology*. 49:219-286.

Anderson, R. T., Vrionis, H. A., Ortiz-Bernad, I., Resch, C. T., Long, P. E., Dayvault, R., Karp, K., Marutzky, S, Metzler, D. R., Peacock, A., White, D. C., Lowe, M. and Lovley, D. R. (2003) Stimulating the in situ activity of *Geobacter* species to remove uranium from the groundwater of a uranium-contaminated aquifer. *Applied Environmental Microbiology*. 69:5884-5891.

D. R. Lovely and J. R. Lloyd (2000) Microbes with a metal for bioremediation, *Nat. Biotechnol.* 18, pp. 600-601.

Sani, R. K., B. Peyton, W. Smith, W. Apel, and J. Petersen. (2002) Dissimilatory reduction of Cr(VI), Fe(III), and U(VI) by *Cellulomonas* isolates". *Appl. Microbiol. Biotechnol.* 60:192-199, Van Heerden, E., Opperman, D. J., Bester, P. A., van Marwijk, J., Cason, E. D., Litthauer, D., Piater, L. A. and Onstott, T. C. (2008) Metabolic promiscuity from the deep subsurface: A story of Survival or Superiority. *Proceedings of SPIE—The International Society for Optical Engineering* 7097:70970 S, Haas, J. R. and Northup, A. (2004) Effects of aqueous complexation on reductive precipitation of uranium by *Shewanella putrefaciens*. *Geochemical Transactions*. 5:41-48.

Kieft, T. L., Fredrickson, J. K., Onstott, T. C., Gorby, Y. A., Kostandarithes, H. M., Bailey, T. J., Kennedy, D. W., Li, S. W., Plymale, A. E., Spadoni, C. M. and Gray, M. S. (1999) Dissimilatory reduction of Fe(III) and other electron acceptors by a *Thermus* isolate. *Applied Environmental Microbiology*. 65:1214-1221.

Kaufmann, F., and Lovley, D. (2001) Isolation and characterization of a soluble NADPH-dependant Fe(III) reductase from *Geobacter sulfurreducens*. *Journal of Biotechnology*. 183: 4468-4467

Johnson, D. A. and Florence, T. M. (1971) Spectrophotometric determination of uranium(VI) with 2-(5-bromo-2-pyridylazo)-5-diethylaminophenol. *Analitica Chimica. Acta*. 53:73-79.

Li, X and Krumholtz X. R. (2009) Thioredoxin is Involved in U(VI) and Cr(VI) Reduction in *Desulfovibrio desulfuricans* G20. *Journal of bacteriology*. 191: 4924-4933.

Hua, B., Xu, H., Terry, J. and Deng, B. (2006) Kinteics of uranium(VI) rduction by hydrogen sulphide in anoxic aqu\ueous systems. *Environmental Science and Technology*. 49:4666-4671.

The invention claimed is:

1. An isolated polypeptide derived from *Thermus scotoductus* strain SA-01 that is responsible for the reduction of uranium (VI), in a source of uranium (VI), to uranium (IV), wherein the polypeptide comprises the amino acid sequence of SEQ ID No: 1.

2. The polypeptide according to claim 1, wherein the polypeptide is a homogenous protein, having an apparent molecular weight of 70 kDa, as determined by SDS-PAGE.

3. A recombinant plasmid comprising an isolated nucleic acid molecule coding for the amino acid sequence of SEQ ID No: 1, or an isolated nucleic acid molecule comprising the nucleotide sequence of SEQ ID No: 2, and a nucleotide sequence heterologous to SEQ ID NO:2.

4. A vector comprising an isolated nucleic acid coding for the amino acid sequence of SEQ ID No: 1, or an isolated nucleic acid molecule comprising the nucleotide sequence of SEQ ID No: 2.

5. A host cell comprising the vector according to claim 4.

6. A method for producing a polypeptide, that is responsible for the reduction of uranium (VI), in a source of uranium (VI), to uranium (IV), the method including the steps of:
a) transfecting a host cell with an isolated nucleic acid molecule coding for the amino acid sequence of SEQ ID No: 1, or an isolated nucleic acid molecule comprising the nucleotide sequence of SEQ ID No: 2;
b) culturing the host cell so as to express the polypeptide of SEQ ID NO: 1 in the host cell; and
c) optionally, isolating and purifying the polypeptide of SEQ ID NO: 1.

7. A microorganism transformed with an isolated nucleic acid molecule coding for the amino acid sequence of SEQ ID No: 1, or an isolated nucleic acid molecule comprising the nucleotide sequence of SEQ ID No: 2.

8. A method of using a polypeptide according to claim 1 in the reduction of uranium (VI), in a source of uranium (VI), to uranium (IV), comprising contacting the uranium (VI) with a polypeptide according to claim 1, whereby the uranium (VI) is reduced to uranium (IV).

9. A method of using a microorganism according to claim 7 in the bioremediation, or at least partial bioremediation, of a U (VI) contaminated site or of U (VI) contaminated environmental media, comprising introducing a microorganism according to claim 7 to a U (VI) contaminated site or a U (VI) contaminated environmental media, whereby bioremediation is initiated.

* * * * *

UNITED STATES PATENT AND TRADEMARK OFFICE
CERTIFICATE OF CORRECTION

PATENT NO. : 8,685,688 B2  Page 1 of 1
APPLICATION NO. : 13/497407
DATED : April 1, 2014
INVENTOR(S) : Cason et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this

Twenty-ninth Day of September, 2015

Michelle K. Lee
*Director of the United States Patent and Trademark Office*